(12) United States Patent
Madi et al.

(10) Patent No.: US 12,233,053 B2
(45) Date of Patent: Feb. 25, 2025

(54) ADENOSINE A3 RECEPTOR ANTAGONISTS FOR TREATING AGING SKIN AND WOUNDS

(71) Applicant: ORADIN PHARMACEUTICAL LTD., Tel Aviv (IL)

(72) Inventors: Lea Levana Madi, Moshav Mahseya (IL); Rafi Korenstein, Tel Aviv (IL)

(73) Assignee: ORADIN PHARMACEUTICAL LTD., Tel Aviv (IL)

( * ) Notice: Subject to any disclaimer, the term of this patent is extended or adjusted under 35 U.S.C. 154(b) by 0 days.

(21) Appl. No.: 18/558,454

(22) PCT Filed: May 3, 2022

(86) PCT No.: PCT/IL2022/050458
§ 371 (c)(1),
(2) Date: Nov. 1, 2023

(87) PCT Pub. No.: WO2022/234576
PCT Pub. Date: Nov. 10, 2022

(65) Prior Publication Data
US 2024/0216351 A1    Jul. 4, 2024

Related U.S. Application Data

(60) Provisional application No. 63/183,646, filed on May 4, 2021.

(51) Int. Cl.
*A61K 31/4418*    (2006.01)
*A61K 8/49*    (2006.01)
(Continued)

(52) U.S. Cl.
CPC ........ *A61K 31/4418* (2013.01); *A61K 8/4933* (2013.01); *A61P 17/02* (2018.01); *A61Q 19/08* (2013.01)

(58) Field of Classification Search
CPC .............. A61K 31/4418; A61K 8/4933; A61K 2800/782; A61K 8/4926; A61P 17/02; A61Q 19/08
(Continued)

(56) References Cited

U.S. PATENT DOCUMENTS 6,448,253 B1    9/2002    Baraldi et al.
7,470,698 B2    12/2008    Baraldi et al.
(Continued)

FOREIGN PATENT DOCUMENTS

EP    1428522 A1    6/2004
EP    1424064 B1    6/2007
(Continued)

OTHER PUBLICATIONS

Paoletta et al ,Receptor-Driven Identification of Novel Human A3 Adenosine , Methods in Enzymology, vol. 485, 2010 Elsevier Inc., pp. 225-244) (Year: 2010).*
(Continued)

*Primary Examiner* — Taylor V Oh
(74) *Attorney, Agent, or Firm* — Allan A. Fanucci

(57) ABSTRACT

The invention provides a method of improving the appearance of aging skin by administering locally to an area of the aging skin of a subject a cosmetic or dermatological composition that includes an effective amount of an adensoine A3 receptor antagonist and a dermatologically acceptable carrier, thereby improving the appearance of the area of the aging skin.

14 Claims, 9 Drawing Sheets

(51) Int. Cl.
*A61P 17/02* (2006.01)
*A61Q 19/08* (2006.01)

(58) Field of Classification Search
USPC .......................................................... 514/356
See application file for complete search history.

(56) References Cited

U.S. PATENT DOCUMENTS

| 7,767,686 | B2 | 8/2010 | Podhajsky |
| 8,088,369 | B2 | 1/2012 | Izawa et al. |
| 2006/0128652 | A1 | 6/2006 | Jagtap et al. |
| 2010/0168049 | A1 | 7/2010 | Laboureau et al. |
| 2012/0134945 | A1 | 5/2012 | Madi et al. |

FOREIGN PATENT DOCUMENTS

| EP | 2204154 A1 | 7/2010 |
| WO | 2008/001921 A2 | 1/2008 |
| WO | 2011/010306 A1 | 1/2011 |

OTHER PUBLICATIONS

Abella (2006), "Evaluation of anti-wrinkle efficacy of adenosine-containing products using the FOITS technique." Int J Cosmet Sci 28(6): 447-451.

Barkan et al. (2020), "Pharmacological characterization of novel adenosine A3 receptor antagonists." Sci Rep 10(1): 20781 (21 pages).

Che et al. (2007), "Adenosine A2A Receptor Occupancy Stimulates Collagen Expression by Hepatic Stellate Cells via Pathways Involving Protein Kinase A, Src, and Extracellular Signal-Regulated Kinases 1/2 Signaling Cascade or p38 Mitogen-Activated Protein Kinase Signaling Pathway." Mol Pharmacol 72(6): 1626-1636.

Choi et al. (2014), "Melanosome uptake is associated with the proliferation and differentiation of keratinocytes." Arch Dermatol Res 306(1): 59-66.

Faghihi et al. (2013) "Comparison of the Efficacy of Topical Minoxidil 5% and Adenosine 0.75% Solutions on Male Androgenetic Alopecia and Measuring Patient Satisfaction Rate." Acta Dermatovenerol Croat 21(3): 155-159.

Fishman et al. (2012), "Pharmacological and therapeutic effects of A3 adenosine receptor agonists." Drug Discov Today 17(7-8): 359-366.

"Ingredient Spotlight: Adenosine," (https://soonskincare.com/blogs/news/ingredient-spotlight-adenosine): Admin Soon Skincare (Blog); Mar. 16, 2019 (2 pages).

Kim et al. (2019), "Anti-Aging Potential of Substance P-Based Hydrogel for Human Skin Longevity." Int J Mol Sci 20(18): 4453 (14 pages).

Lee et al. (2012), "Valproic Acid Induces Cutaneous Wound Healing In Vivo and Enhances Keratinocyte Motility." PLoS One 7(11): e48791 (10 pages).

Montesinos et al. (2002), "Adenosine Promotes Wound Healing and Mediates Angiogenesis in Response to Tissue Injury Via Occupancy of A(2A) Receptors." Am J Pathol 160(6): 2009-2018.

Montesinos et al. (2015), "Promotion of Wound Healing by an Agonist of Adenosine A2A Receptor Is Dependent on Tissue Plasminogen Activator." Inflammation 38(6): 2036-2041.

Rivera-Oliver et al. (2014), "Using caffeine and other adenosine receptor antagonists and agonists as therapeutic tools against neurodegenerative diseases: A review." Life Sci 101(1-2): 1-9.

Shin et al. (2015), "Protease-Activated Receptor-2 Is Associated with Terminal Differentiation of Epidermis and Eccrine Sweat Glands." Ann Dermatol 27(4): 364-370.

Valls et al. (2009), "Adenosine receptor agonists for promotion of dermal wound healing." Author Manuscript. Published in final edited form as: Biochem Pharmacol. Apr. 1, 2009; 77(7): 1117-1124.

Victor-Vega et al. (2002), "Adenosine A2A Receptor Agonists Promote More Rapid Wound Healing than Recombinant Human Platelet-Derived Growth Factor (Becaplermin Gel)." Inflammation 26(1): 19-24.

Yeo et al. (2020), "Design and Characterization of Elastic Artificial Skin Containing Adenosine-Loaded Solid Lipid Nanoparticles for Treating Wrinkles." Pharmaceutics 13(1): 33 (26 pages).

"Why Adenosine Is the Next Anti-Aging Ingredient, You Should Know About." (https://thedermreview.com/adenosine/) by Elle MacLeman, Sep. 9, 2020 (4 pages).

International Search Report, PCT/IL2022/050458, dated Aug. 14, 2022.

International Written Opinion of the International Searching Authority, PCT/IL2022/050458, dated Aug. 14, 2022.

* cited by examiner

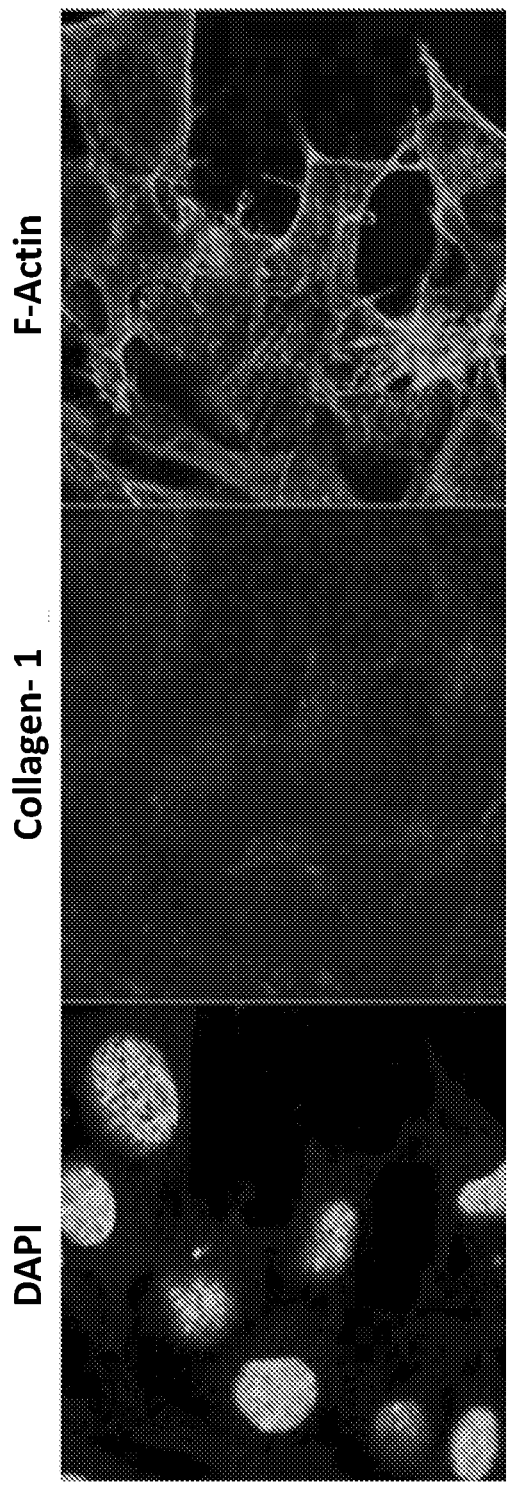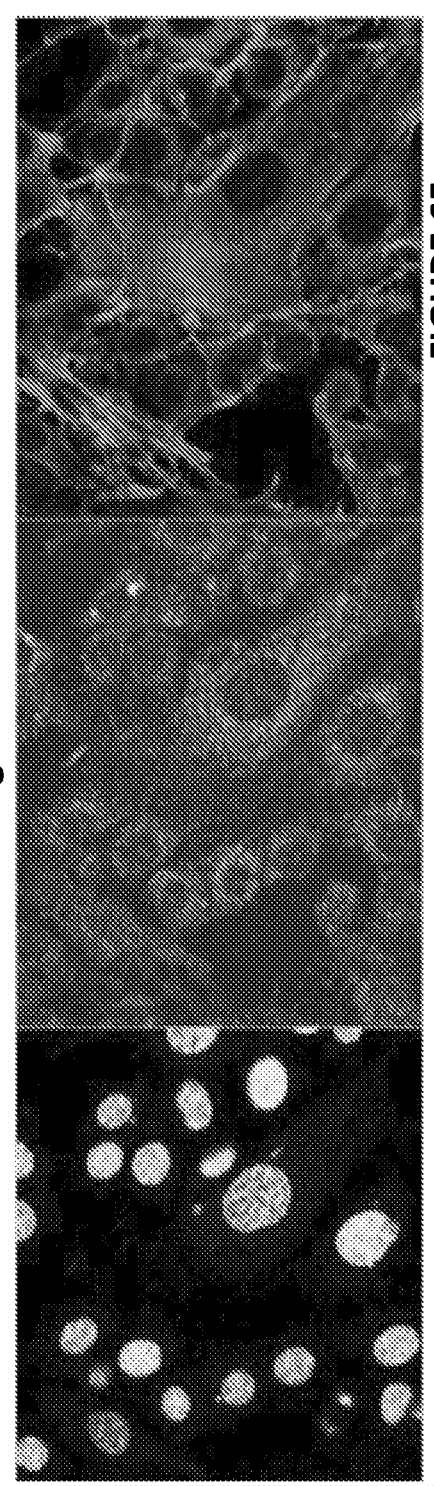

Control

MRS-1523

PAR-2

MRS-1523

Control

FLG

ADENOSINE A3 RECEPTOR ANTAGONISTS FOR TREATING AGING SKIN AND WOUNDS

CROSS-REFERENCE TO RELATED APPLICATIONS

This application is a 371 filing of International Patent Application PCT/IL2022/050458 filed May 3, 2022, which claims the benefit of application No. 63/183,646 filed May 4, 2021.

FIELD OF THE INVENTION

The present invention relates to cosmetic, dermatological or pharmaceutical compositions comprising adenosine A3 receptor antagonists for use in improving the appearance of aging skin, particularly wrinkled skin, and in treating wounds, particularly chronic wounds.

BACKGROUND OF THE INVENTION

Skin homeostasis is mediated by a complex paracrine network between the different skin cell types which is modulated by growth factors and cytokines. Defects in cytokine and growth factor signal pathways play a key role in perturbing the proliferation and differentiation balance of skin cells.

The outer layer of the skin is the epidermis. Human epidermis is a constantly self-renewing and differentiating structure, composed mainly of keratinocytes. Keratinocytes undergo a differentiation program tightly associated with their movement from the innermost basal layer to the outer suprabasal layer and with changes in their cell-cell adhesion profile, resulting in the formation of the protective outer layer of the epidermis, the stratum corneum. The commencement of keratinocyte differentiation is regulated by multiple effectors, including Ca++ gradient, UV exposure, and drugs.

Skin aging occurs due to internal processes and factors, i.e., cellular metabolism, hormonal changes, and genetic mutations, and due to external factors, i.e., toxins, chemicals, and ultraviolet (UV) radiation. Aged skin is biologically characterized by a general decline of extracellular matrix (ECM) components, particularly associated with disorganization and decrease of collagen and elastin. Increased inflammatory processes also characterize aging skin, causing wrinkling and thinning of the dermis and epidermis. Pro-inflammatory mediators, released from inflammatory cells, enhance the activation of collagenases, thus leading to collagen degradation (Da Jung et al., (2019) Int. J. Mol. Sci. 20(18): 4453).

Cutaneous wound healing is a complex process involving re-epithelialization, granulation tissue formation, and tissue remodeling in all skin components, including the epidermis, dermis, hypodermis, blood vessels, and connective tissue, leading to wound closure and repair of tissues. Typically, wound healing process can be divided into four phases: clotting/hemostasis phase, the inflammatory phase, the proliferative phase, and the remodeling phase.

Fibroblasts in the dermis and keratinocytes in the epidermis are the most important cells acting in wound healing and in anti-aging and play an important role in tissue regeneration. While keratinocytes serve as a protecting layer of the skin from most of the external injuries, fibroblasts have a crucial function in wound healing and in attenuating skin aging processes which require collagen production for replacing the degraded collagen at the wound site or at the wrinkles.

Drugs which promote keratinocyte and fibroblast viability and increase cell migration to the wounded area were shown to be effective in wound healing (Soung-Hoon et al., (2012) Plos One. (11) e48791). Also, drugs which activate fibroblasts in the dermis and stimulate collagen production were demonstrated to diminish wrinkles and to promote wound healing (Da Jung et al. 2019, ibid).

The role of adenosine released from injured or ischemic tissues in wound healing and in tissue repair was demonstrated. Recent studies in genetically manipulated mice showed that adenosine receptors are required for appropriate granulation tissue formation and for adequate wound healing. Adenosine A2A and A2B receptors were shown to be involved in stimulating new ECM production and in angiogenesis, both processes are critical in granulation tissue formation. Adenosine A1 receptors were also suggested to contribute to new vessel formation. The binding of adenosine to these receptors was shown to induce endothelial cell proliferation and to stimulate angiogenic factor production by endothelial cells and by other cells present in the wound (Montesinos et al. (2002) Amer. J. Pathol. 160: 2009-2018).

Adenosine applied topically has been used to promote hair growth and skin health. For the treatment of androgenetic alopecia, adenosine (0.75% solution) displayed efficacy similar to minoxidil but was preferred by patients because of the rapid response and its efficacy (Faghihi, G. et al. (2013) Acta Dermatovenerol. Croat. 21: 155-159). Applied in cosmetic reparations (0.1% cream or 1% dissolvable film) for 2 months, adenosine significantly improved skin smoothness and reduced facial wrinkles (Abella, M. L. (2006) Int. J. Cosmetic Sci 28447-451). Sonedenoson (MRE-0094) 23, agonist to adenosine A2A receptor, was shown to be effective in the treatment of poorly healing wounds in animal models (Victor-Vega (2002) Inflammation 26: 19-24). The effect of adenosine A2A receptor agonist was found to be dependent on tissue plasminogen activator (Montesinos et al., (2015) Inflammation 38: 2036-2041).

Signaling pathways crucial for cutaneous wound healing include Wnt, extracellular signal-regulated kinase (ERK), and phosphatidylinositol 3-kinase (PI3-kinase) signaling pathways. Growth factors such as epidermal growth factor (EGF) and basic fibroblast growth factor (bFGF) accelerate keratinocyte migration and epithelialization in skin wound healing by activating the ERK and PI3-kinase/Akt signaling pathways. Conversely, inhibition of these signaling pathways was shown to impair corneal wound healing. These results indicated that Wnt, ERK and PI3-kinase/Akt signaling pathways may be useful therapeutic targets to enhance wound healing. It was also demonstrated that adenosine A2A receptor occupancy stimulated collagen expression via protein kinase A, Src, and extracellular signal-regulated kinases 1/2 signaling cascade or p38 mitogen-activated protein kinase signaling pathway (Che et al., (2007) Molecular Pharmacology 72: 1626-1636).

U.S. Pat. No. 7,767,686 to Podhajsky discloses methods of treating symptoms associated with an elevated concentration of adenosine due to an ablation procedure, the methods comprises administering to a mammalian subject undergoing the ablation procedure one or more adenosine receptor antagonists such as 8SPT, MRS1754, MRS1220, MRE3008F20, MRS1523, ATL146e, or combinations thereof, in an amount effective in preventing or alleviating the symptoms associated with the elevated concentration of adenosine.

WO 2011/010306 to the inventors of the present invention discloses pharmaceutical and cosmetic compositions comprising A3 adenosine receptor ligands and methods of use thereof for modulating melanin production, secretion and/or accumulation in skin.

There is still an unmet need for improved methods for delaying or preventing aging of skin. There is also an unmet need for improved methods for promoting wound healing.

SUMMARY OF THE INVENTION

The present invention provides method of increasing expression of collagen in aging skin comprising administering locally to an area of the aging skin of a subject a cosmetic or dermatological composition comprising an effective amount of an adenosine A3 receptor antagonist and a dermatologically acceptable carrier, thereby increasing the expression of collagen in the area of said aging skin. The methods are useful for improving the appearance of the aging skin.

The present invention further provides methods of treating a wound comprising administering locally to a wound site of a subject in need of such treatment a pharmaceutical composition comprising an effective amount of an adenosine A3 receptor antagonist and a pharmaceutically acceptable carrier, thereby treating the wound.

It is now disclosed for the first time that an adenosine A3 receptor antagonist, e.g., 3-propyl-6-ethyl-5[(ethylthio)carbonyl]-2-phenyl-4-propyl-3-pyridine carboxylate (MRS-1523), promoted the migration of both keratinocyte cells and fibroblast cells under in vitro conditions. It is further disclosed that MRS-1523 simulated the proliferation of keratinocyte cells, while inhibiting their differentiation, as detected under in vitro conditions.

The present invention further discloses the unexpected findings that MRS-1523 increased the expression of collagen-1 in human skin explants and augmented the number of fibroblast cells in these MRS-1523 treated skin explants. MRS-1523 was also shown to increase collagen expression in fibroblast cells in culture.

It is further disclosed while MRS-1523 was shown to be highly effective in promoting the migration of keratinocyte cells and fibroblast cells, this antagonist attenuated the migration of melanocytes. The effects of MRS-1523 were observed at nanomolar concentrations to up to 10 μM, at which concentrations MRS-1523 did not exert any toxic effects.

The present invention therefore shows that MRS-1523, by virtue of its stimulatory effect on keratinocyte and fibroblast cell migration, by virtue of its promoting effect on collagen expression in skin, and by virtue of its inhibitory effect on keratinocyte differentiation, can be highly effective in decreasing or diminishing different signs of aging skin, such as wrinkles, saggy skin, wizened skin, and thinned skin. The beneficial effects of MRS-1523 on keratinocyte and fibroblast cells can be also useful for promoting wound healing, particularly of chronic wounds.

Thus, the compositions of the present invention which comprise as an active agent an adenosine A3 receptor antagonist, such as MRS-1523, can be highly advantageous for cosmetic use in order to improve the appearance of aging skin and for therapeutic use in order to promote wound healing.

According to a first aspect, the present invention provides a method of promoting expression of collagen in aging skin comprising administering locally to an area of the aging skin of a subject a cosmetic or dermatological composition comprising an effective amount of an adenosine A3 receptor antagonist and a dermatologically acceptable carrier, thereby promoting the expression of collagen in the area of said aging skin.

According to some embodiments, the method of promoting collagen expression is useful for improving the appearance of the aging skin.

According to additional embodiments, the aging skin is facial skin, neck skin, hand skin, or any combination thereof. According to certain embodiments, the aging skin is facial skin and/or neck skin.

According to further embodiments, the aging skin is selected from the group consisting of wrinkled skin, wizened skin, slaggy skin, thinned skin, and any combination thereof. Each possibility represents a separate embodiment of the invention.

According to yet further embodiments, the wrinkled skin is selected from the group consisting of skin comprising wrinkles, skin comprising fine lines, skin comprising coarse deep lines, and any combination thereof. Each possibility represents a separate embodiment of the invention.

According to some embodiments, the adenosine A3 receptor antagonist is selected from the group consisting of pyridines, dihydropyridines, isoquinolines, triazoloquinazolines thiazolopyrimidines, imidazoquinolines, triazolopurines, deazapurines, triazolonaphthiridines, flavonoids, xanthines, pyrazolo-triazolo-pyrimidines, triazolo-triazolo-pyrimidines, imidazolo-triazolo-pyrimidines, and derivatives thereof. Each possibility represents a separate embodiment of the invention.

According to certain embodiments, the adenosine A3 receptor antagonist is selected from the group consisting of 3-propyl-6-ethyl-5[(ethylthio)carbonyl]-2-phenyl-4-propyl-3-pyridine carboxylate (MRS-1523); 1,4-dihydro-2-methyl-6-phenyl-4-(phenylethynyl)-3,5-pyridinedicarboxylic acid 3-ethyl-5-[(3-nitrophenyl)methyl] ester (MRS-1334); 3-ethyl-5-benzyl-2-methyl-4-phenylethynyl-6-phenyl-1,4-(±)-dihydropyridine-3,5 dicarboxylate (MRS-1191); and 3-ethyl-5-benzyl-2-methyl-6-phenyl-4-styryl-1,4-(±)-dihydropyridine-3,5-dicarboxylate (MRS-1097). Each possibility represents a separate embodiment of the invention.

According to an exemplary embodiment, the adenosine A3 receptor antagonist is 3-propyl-6-ethyl-5[(ethylthio)carbonyl]-2-phenyl-4-propyl-3-pyridine carboxylate (MRS-1523).

According to some embodiments, the cosmetic or dermatological composition further comprises one or more excipients selected from the group consisting of emulsifying agents, pH buffering agents, preservatives, chelating agents, tonicity agents, humectants, antioxidants, and gelling agents.

According to additional embodiments, the cosmetic or dermatological composition is in the form selected from the group consisting of a solution, emulsion, nanoemulsion, suspension, microparticles, ointment, cream, lotion, paste, gel, hydrogel, spray, powder, stick, and a patch. Each possibility represents a separate embodiment of the invention.

According to further embodiments, the cosmetic or dermatological composition is administered topically. According to certain embodiments, if the cosmetic or dermatological composition is administered topically, said composition is in the form of an ointment, cream, lotion, paste, gel, hydrogel, spray, powder, stick, or a patch.

According to yet further embodiments, the cosmetic or dermatological composition is administered by injection. According to still further embodiments, the injection is intraepidermal injection, intradermal injection, subcutaneous injection, micro-injection, or any combination thereof. According to certain embodiments, if the cosmetic or dermatological composition is administered by injection, said composition is in the form of a solution, emulsion suspension, or microparticles.

According to some embodiments, the cosmetic or dermatological composition is administered at least once a day for at least one week, at least one month, at least three months, at least six months, at least one year, or as required.

According to another aspect, the present invention provides a method of treating a wound comprising administering locally to a wound site of a subject in need of such treatment a pharmaceutical composition comprising an effective amount of an adenosine A3 receptor antagonist and a pharmaceutically acceptable carrier.

According to some embodiments, the wound is a chronic wound.

According to further embodiments, the chronic wound is selected from the group consisting of a diabetic ulcer, a venous stasis ulcer, an arterial insufficiency ulcer, a pressure ulcer, a chronic post-operative wound, and a chronic post trauma wound. Each possibility represents a separate embodiment of the invention.

According to some embodiments, the adenosine A3 receptor antagonist is selected from the group consisting of pyridines, dihydropyridines, isoquinolines, triazoloquinazolines thiazolopyrimidines, imidazoquinolines, triazolopurines, deazapurines, triazolonaphthiridines, flavonoids, xanthines, pyrazolo-triazolo-pyrimidines, triazolo-triazolo-pyrimidines, imidazolo-triazolo-pyrimidines, and derivatives thereof. Each possibility represents a separate embodiment of the invention.

According to certain embodiments, the adenosine A3 receptor antagonist is selected from the group consisting of 3-propyl-6-ethyl-5[(ethylthio)carbonyl]-2-phenyl-4-propyl-3-pyridine carboxylate (MRS-1523); 1,4-dihydro-2-methyl-6-phenyl-4-(phenylethynyl)-3,5-pyridinedicarboxylic acid 3-ethyl-5-[(3-nitrophenyl)methyl] ester (MRS-1334); 3-ethyl-5-benzyl-2-methyl-4-phenylethynyl-6-phenyl-1,4-(±)-dihydropyridine-3,5 dicarboxylate (MRS-1191); and 3-ethyl-5-benzyl-2-methyl-6-phenyl-4-styryl-1,4-(±)-dihydropyridine-3,5-dicarboxylate (MRS-1097). Each possibility represents a separate embodiment of the invention.

According to an exemplary embodiment, the adenosine A3 receptor antagonist to be used for treating a wound, particularly a chronic wound, is 3-propyl-6-ethyl-5[(ethylthio)carbonyl]-2-phenyl-4-propyl-3-pyridine carboxylate (MRS-1523).

According to some embodiments, the pharmaceutical composition further comprises one or more excipients selected from the group consisting of emulsifying agents, pH buffering agents, preservatives, chelating agents, tonicity agents, humectants, antioxidants, and gelling agents.

According to additional embodiments, the pharmaceutical composition is in the form selected from the group consisting of a solution, emulsion, nanoemulsion, suspension, microparticles, ointment, cream, lotion, paste, gel, hydrogel, spray, powder, stick, and a patch. Each possibility represents a separate embodiment of the invention.

According to further embodiments, the pharmaceutical composition is administered topically.

According to yet further embodiments, the pharmaceutical composition is administered at least once a day for at least one week, at least one month, or at least 3 months.

According to another aspect, the present invention provides a method of improving the appearance of aging skin comprising administering locally to an area of the aging skin of a subject a cosmetic or dermatological composition comprising an effective amount of an adensoine A3 receptor antagonist and a dermatologically acceptable carrier.

According to some embodiments, the aging skin is facial skin, neck skin, hand skin, or any combination thereof. According to certain embodiments, the aging skin is facial skin and/or neck skin.

According to additional embodiments, the aging skin is selected from the group consisting of wrinkled skin, wizened skin, slaggy skin, thinned skin, and any combination thereof. Each possibility represents a separate embodiment of the invention.

According to further embodiments, the wrinkled skin is selected from the group consisting of skin comprising wrinkles, skin comprising fine lines, skin comprising coarse deep lines, and any combination thereof. Each possibility represents a separate embodiment of the invention.

According to some embodiments, the adenosine A3 receptor antagonist is selected from the group consisting of pyridines, dihydropyridines, isoquinolines, triazoloquinazolines thiazolopyrimidines, imidazoquinolines, triazolopurines, deazapurines, triazolonaphthiridines, flavonoids, xanthines, pyrazolo-triazolo-pyrimidines, triazolo-triazolo-pyrimidines, imidazolo-triazolo-pyrimidines, and derivatives thereof. Each possibility represents a separate embodiment of the invention.

According to certain embodiments, the adenosine A3 receptor antagonist is selected from the group consisting of 3-propyl-6-ethyl-5[(ethylthio)carbonyl]-2-phenyl-4-propyl-3-pyridine carboxylate (MRS-1523); 1,4-dihydro-2-methyl-6-phenyl-4-(phenylethynyl)-3,5-pyridinedicarboxylic acid 3-ethyl-5-[(3-nitrophenyl)methyl] ester (MRS-1334); 3-ethyl-5-benzyl-2-methyl-4-phenylethynyl-6-phenyl-1,4-(±)-dihydropyridine-3,5 dicarboxylate (MRS-1191); and 3-ethyl-5-benzyl-2-methyl-6-phenyl-4-styryl-1,4-(±)-dihydropyridine-3,5-dicarboxylate (MRS-1097). Each possibility represents a separate embodiment of the invention.

According to an exemplary embodiment, the adenosine A3 receptor antagonist to be used for improving the appearance the aging skin is 3-propyl-6-ethyl-5[(ethylthio)carbonyl]-2-phenyl-4-propyl-3-pyridine carboxylate (MRS-1523).

According to some embodiments, the cosmetic or dermatological composition further comprises one or more excipients selected from the group consisting of emulsifying agents, pH buffering agents, preservatives, chelating agents, tonicity agents, humectants, antioxidants, and gelling agents.

According to additional embodiments, the cosmetic or dermatological composition is in the form selected from the group consisting of a solution, emulsion, nanoemulsion, suspension, microparticles, ointment, cream, lotion, paste, gel, hydrogel, spray, powder, stick, and a patch. Each possibility represents a separate embodiment of the invention.

According to further embodiments, the cosmetic or dermatological composition is administered topically. According to certain embodiments, if the cosmetic or dermatological composition is administered topically, said composition is in the form of an ointment, cream, lotion, paste, gel, hydrogel, spray, powder, stick, or a patch.

According to yet further embodiment, the cosmetic or dermatological composition is administered by injection. According to still further embodiments, the injection is intraepidermal injection, intradermal injection, subcutaneous injection, micro-injection, or any combination thereof. According to certain embodiments, if the cosmetic or dermatological composition is administered by injection, said composition is in the form of a solution, emulsion suspension, or microparticles.

According to some embodiments, the cosmetic or dermatological composition is administered at least once a day for at least one week, at least one month, at least three months, at least six months, at least one year, or as required.

According to another aspect, the present invention provides a cosmetic or dermatological composition comprising an effective amount of an adenosine A3 receptor antagonist and a dermatologically acceptable carrier for use in promoting expression of collagen in aging skin of a subject, wherein the cosmetic or dermatological composition is adapted to be administered locally to an area of the aging skin according to the principles of the present invention.

According to a further aspect, the present invention provides a pharmaceutical composition comprising an adenosine A3 receptor antagonist and a pharmaceutically acceptable carrier for use in treating a wound in a subject, wherein the pharmaceutical composition is adapted to be administered locally to a wound site of the subject according to the principles of the present invention.

According to another aspect, the present invention provides a cosmetic or dermatological composition comprising an adenosine A3 receptor antagonist and a dermatologically acceptable carrier for use in improving the appearance of aging skin in a subject, wherein wherein the cosmetic or dermatological composition is adapted to be administered locally to an area of the aging skin according to the principles of the present invention.

These and other embodiments of the present invention will be better understood in relation to the description, examples and claims that follow.

BRIEF DESCRIPTION OF THE FIGURES

FIGS. 4A-B show bar graphs of the gap size of HaCaT keratinocyte cells (A) and 3T3 fibroblast cells (B) 24 hours after treatment with increasing concentrations of MRS-1523 in the scratch assay. FIGS. 4C-E show bar graphs of the gap size of HaCAT cells (FIG. 4C), 3T3 fibroblasts (FIG. 4D), and B16-F1 melanocytes (FIG. 4E) after 24-hour treatment with 10 μM MRS-1523 in the scratch assay. *$p<0.05$, **$p<0.01$ by Student T-test.

FIGS. 5A and 5B show histological sections of untreated skin explants stained with H&E (FIG. 5A) or with Fontana Masson (FIG. 5B). FIGS. 5C and 5D show histological sections of skin explants which were treated with MRS-1523 and stained with H&E (FIG. 5C) or with Fontana Masson (FIG. 5D). Arrow indicates fibroblast staining.

FIGS. 6A-F show the expression of collagen-1 and F-actin in 3T3 fibroblast cells treated with MRS-1523 as compared to untreated cells. 3T3 fibroblast cells were treated in culture with MRS-1523 (10 μM) for 24 hours, and confocal fluorescence images of the cell nuclei stained with DAPI (blue; FIG. 6D), and of the cells stained for collagen-1 (green, FIG. 6E), or for F-actin (red; FIG. 6F) are presented. Confocal fluorescence images of nuclei of control untreated 3T3 fibroblast cells stained with DAPI (blue; FIG. 6A), and of control fibroblast cells stained for collagen-1 (FIG. 6B), or for F-actin (red; FIG. 6C) are also presented.

FIGS. 7A and 7B, respectively), and for the expression of Filaggrin (FLG; FIG. 7C and FIG. 7D, respectively).

DETAILED DESCRIPTION OF THE INVENTION

Figure 2:
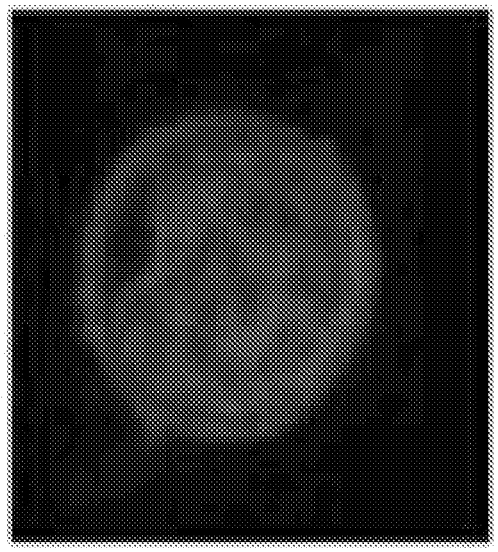
FIG. 2 shows the expression of protease-activated receptor-2 (PAR-2) in HaCaT keratinocytes. Confocal fluorescence image of PAR-2 (red) and DAPI (blue) in HaCaT cells is shown.

The present invention provides cosmetic or dermatological compositions comprising an effective amount of an adenosine A3 receptor antagonist and a dermatologically acceptable carrier for use in promoting expression of collagen in aging skin of a subject, wherein the cosmetic and dermatological compositions are adapted to be administered locally to an area of the aging skin. The compositions are particularly useful for improving the appearance of aging skin.

The present invention further provides pharmaceutical compositions comprising an effective amount of an adenosine A3 receptor antagonist and a pharmaceutically acceptable carrier for use in treating a wound, wherein the compositions are adapted to be administered locally to a wound site of a subject. Particularly, the wound is a chronic wound.

The present invention provides cosmetic or dermatological compositions comprising an effective amount of an adenosine A3 receptor antagonist and a dermatologically acceptable carrier for use in improving the appearance of aging skin, wherein aging of the skin is associated with or affected by a decrease in collagen content in said skin, and wherein the compositions are adapted to be applied locally to an area of the aging skin.

Compositions

The present invention provides cosmetic, dermatological or pharmaceutical compositions comprising as an active agent an adenosine A3 receptor antagonist and a dermatologically or pharmaceutically acceptable carrier.

The terms "cosmetic composition" and "dermatological composition" are used interchangeably throughout the specification and claims and refer to a composition suitable for treating a skin condition, particularly aging skin.

The term "pharmaceutical composition" as used herein refers to a composition suitable for treating a disease or disorder, particularly a wound, more particularly a chronic wound. For brevity, the cosmetic or dermatological composition and the pharmaceutical composition are referred to as "composition(s)".

The term "adenosine A3 receptor antagonist" refers to any compound capable of specifically binding to the adenosine A3 receptor (A3R), and capable of fully or partially inhibiting the activation of said receptor. The adenosine A3 receptor antagonist is thus a compound that exerts its prime effect though the binding to the A3R.

The ability of adenosine A3 receptor antagonist to bind to A3R may be assessed in competitive binding assays or in functional assays as known in the art. For example, a test compound can be assessed in a competitive binding assay for its ability to displace a radiolabeled form of a known adenosine receptor antagonist from binding to the A3R present on cells or membranes. Functional assays can assess the ability of the antagonist to inhibit downstream signaling events, in particular the effect on adenylate cyclase by measuring the effect on cAMP level (i.e., increase or decrease).

According to some embodiments, the adenosine A3 receptor antagonist has a binding affinity (Ki) to the adenosine A3 receptor that is less than about 200 nM, preferably less than about 100 nM, more preferably less than about 50 nM, even more preferably less than 10 nM. According to additional embodiments, the binding affinity of the A3 adenosine receptor antagonist to the adenosine A3 receptor is at least 20 times greater than the binding affinity of said antagonist to the A1 adenosine receptor.

According to some embodiments, the adenosine A3 receptor antagonist is a compound selected from the group consisting of pyridines, dihydropyridines, isoquinolines, triazoloquinazolines thiazolopyrimidines, imidazoquinolines, triazolopurines, deazapurines, triazolonaphthiridines, flavonoids, xanthines, 2-arylpyrazolo[3,4-c]quinoline, 5-N-(phenylcarbamoyl)amino-8-2-(2-furyl)pyrazolo[4,3-e]-1,2,4-triazolo[1,5-c]pyrimidine, pyrazolo-triazolo-pyrimidines, triazolo-triazolo-pyrimidines, imidazolo-triazolo-pyrimidines, and derivatives thereof (see, for example, U.S. Pat. Nos. 6,448,253, 7,470,698, and 7,767,686, the content of which is incorporated by reference as if fully set forth herein). Each possibility represents a separate embodiment of the invention.

According to additional embodiments, the adenosine A3 receptor antagonist is selected from the group consisting of 3-propyl-6-ethyl-5[(ethylthio)carbonyl]-2-phenyl-4-propyl-3-pyridine carboxylate (MRS-1523); 1,4-dihydro-2-methyl-6-phenyl-4-(phenylethynyl)-3,5-pyridinedicarboxylic acid 3-ethyl-5-[(3-nitrophenyl)methyl] ester (MRS-1334); 3-ethyl-5-benzyl-2-methyl-4-phenylethynyl-6-phenyl-1,4-(±)-dihydropyridine-3,5 dicarboxylate (MRS-1191); 3-ethyl 5-benzyl-2-methyl-6-phenyl-4-styryl-1,4-(±)-dihydropyridine-3,5-dicarboxylate (MRS-1097); 5-n-butyl-8-(4-trifluoromethylphenyl)-3H-[1,2,4]triazolo-[5,1-i]purine (OT-7999); (2R,3R,4S,5S)-2-[$N^6$-3-iodobenzyl)adenos-9'-yl]-7-aza-1-oxa-6-oxospiro[4,4]-nonan-4,5-diol (MRS-1292); N-(2-methoxyphenyl)-N'-[2-(3-pyridinyl)-4-quinazolinyl]-urea (VUF-5574); (8R)-8-ethyl-1,4,7,8-tetrahydro-4-5H-imidazo[2,1-i]purine-5-one (PSB-11); 2-phenoxy-6-(cyclohexylamino)purine (MRS-3777); 5N-(4-methoxyphenylcarbamoyl)amino-8-propyl-2-(2-furyl)pyrazolo[4,3-e]-1,2,4-triazolo[1,5-c]pyrimidine (MRE3008F20) and derivatives thereof. Each possibility represents a separate embodiment of the present invention.

According to further embodiments, the adenosine A3 receptor antagonist is selected from the group consisting of 3-propyl-6-ethyl-5[(ethylthio)carbonyl]-2-phenyl-4-propyl-3-pyridine carboxylate (MRS-1523); 1,4-dihydro-2-methyl-6-phenyl-4-(phenylethynyl)-3,5-pyridinedicarboxylic acid 3-ethyl-5-[(3-nitrophenyl)methyl] ester (MRS-1334); and 3-ethyl-5-benzyl-2-methyl-4-phenylethynyl-6-phenyl-1,4-(±)-dihydropyridine-3,5 dicarboxylate (MRS-1191).

According to an exemplary embodiment, the adenosine A3 receptor antagonist is 3-propyl-6-ethyl-5[(ethylthio)carbonyl]-2-phenyl-4-propyl-3-pyridine carboxylate (MRS-1523).

The dermatological or pharmaceutical composition further comprises a dermatologically or pharmaceutically acceptable carrier.

The terms "dermatologically acceptable" or "pharmaceutical acceptable" as used herein mean approved by a regulatory agency of the Federal or a state government or listed in the U.S. Pharmacopeia or other generally recognized pharmacopeia for use in humans. The constituents of the cosmetic, dermatological or pharmaceutical compositions of the present invention are all dermatologically or pharmaceutically acceptable agents.

The term "carrier" refers to a diluent, adjuvant, excipient, or vehicle with which the compound is administered. The carriers can be liquids, preferably sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents.

The composition, if desired, can also contain minor amounts of emulsifying agents or pH buffering agents such as acetates, citrates or phosphates. Preservative such as benzyl alcohol or methyl parabens; chelating agents such as ethylenediaminetetraacetic acid; and agents for the adjustment of tonicity such as sodium chloride or dextrose, are also envisioned.

Other optional excipients include, but are not limited to, humectants such as water soluble liquid polyols, e.g., glycerin, propylene glycol, hexylene glycol, butylene glycol, pentylene glycol, dipropylene glycol, and mixtures thereof; antioxidants such as glycolic acid, citric acid, lactic acid, malic acid, mandelic acid, ascorbic acid, sodium bisulfite, vitamin E and derivatives thereof; wetting agents; suspending agents; gelling agents; skin emollients and skin moisturizers; antimicrobial (e.g., antibacterial) agents; antifungals; analgesics; UV absorbers; anti-aging agents; anti-wrinkling agents, wound healing promoters; anti-inflammatory agents; vitamins such as vitamin C, vitamin B, and derivatives thereof; nutrients such as thiamin, riboflavin, niacin, pantothenates, pyridoxine, folic acid, cobalamin, biotin, choline, inositol, carnitine, etc.; amino acids and their derivatives such as alanine, arginine, asparagine, aspartic acid, carnitine, citrulline, cysteine, dimethylglycine, gamma-aminobutyric acid, glutamic acid, glutamine, glutathione, glycine, histidine, isoleucine, leucine, lysine, methionine, ornithine, phenylalanine, praline, serine, taurine, threonine, tryptophan, tyrosine, valine; minerals such as boron, calcium, chromium, cobalt, copper, fluoride, germanium, iodine, iron, lithium, magnesium, manganese, molybdenum, phosphorus, potassium, selenium, silicon, sodium, sulfur, vanadium, zinc; herbal extracts such as green tea, algae, aloe, etc.; retinoids; flavonoids; and mixtures thereof.

The compositions can be in the form of a solution, emulsion (e.g., oil-in-water, water-in-oil-in-water, water-in-oil or oil-in-water-in-oil), nanoemulsion, suspension, microparticles, oil, ointment, cream, lotion, paste, gel, hydrogel, spray, powder, stick, or combinations thereof.

In some embodiments, a tape or other support structure can be applied to the skin, e.g., to a wrinkle or a wound. In some embodiments, the composition is applied to the skin before the tape is placed. In that situation, the tape may be porous or not.

In some embodiments, the tape is a polymer matrix or gel that permits contact of the composition with the skin when the composition is applied over the tape. Such a tape, also designated a patch or transdermal patch, has the added advantage of providing controlled delivery of a compound to the body. Transdermal patches can be made by dissolving or dispersing the compound in the proper medium and then applying it to the tape. Absorption enhancers can also be used to increase the flux of the compound across the skin. The rate of such flux can be controlled by the polymer matrix or gel and optionally by a rate controlling membrane. In one embodiment, the polymer matrix can be hyaluronic acid which has the property of trapping water and forming a gel, thus particularly useful for improving the appearance of a wrinkle or for promoting wound healing.

For topical application, the composition can be formulated in the form of an ointment containing the adenosine A3 receptor antagonist dissolved or suspended in appropriate carriers. Such carriers include, but are not limited to, mineral oils, liquid vaseline, white vaseline, propylene glycol, polyoxyethylene, polyoxypropylene, emulsifier wax, and water. Alternatively, it can be formulated as a cream or lotion containing the adenosine A3 receptor antagonist dissolved or suspended in appropriate carriers. Such carriers include, but are not limited to, mineral oils, sorbitan monostearate, polysorbate 60, cetyl ester wax, cetearyl alcohol, 2-octyl-dodecanol, benzyl alcohol and water.

For injection, the composition can be formulated as a liquid such as a solution, emulsion, suspension; or as a gel. According to preferred embodiments, the composition is a sterile solution or suspension. Acceptable solvents and carriers include, but are not limited to, water, Ringer's solution and isotonic sodium chloride. In addition, sterile oils are often used as a solvent. To this end, any oil may be used, such as mono- and diglycerides. Fatty acids like oleic acid and its glyceride derivatives are also used for preparing injectable compositions, as are pharmaceutically acceptable natural oils like olive oil, castor oil, and in particular their polyoxyethylenated forms. These oily solutions may comprise suspending agents or diluents like carboxymethyl cellulose for the formulation of emulsions and suspensions. Surfactants like Tweens and emulsifiers may also be included. Aqueous or oleaginous suspensions may be formulated by methods well known to one of skill in the art by using wetting agents or dispersants and suspending agents.

As used herein, "microparticles" means polymer or combinations of polymers made into bodies of various sizes. The microparticles can be in any shape, although they are often in substantially spherical shape, in which case the microparticles are referred to as "microspheres" or "microbeads". Incorporation of the active agent into the microparticles can be accomplished by mixing dry microparticles with solutions of the active agent in an aqueous or hydro-organic solution. Before injection or being composed into an injectable composition, the microspheres are sterilized.

To prepare the composition of the present invention, a variety of techniques may be employed. For example, the active agent may be generally incorporated into a dermatologically acceptable carrier in the manner that is usual for the preparation of skin care products. Thus, the active agent may first be dissolved or dispersed in a portion of the water or another solvent or liquid to be incorporated into the dermatologically acceptable carrier. The preferred compositions for use in this manufacturing approach are oil-in-water, water-in-oil, or water-in-oil-in-water emulsions.

In some embodiments, the active agent, with or without excipients, are maintained in a separate state from the carrier, for example, as a dry powder. The intermixing of the desired amount of the active agent with the desired amount of the carrier, performed by the subject immediately prior to application of the cosmetic, dermatological or pharmaceutical composition, ensures that the active agent will retain its maximum efficacy, and will also permit the potency of the composition to be tailored to the individual needs of the subject. The resulting cosmetic, dermatological or pharmaceutical composition may be then applied to the skin.

The dosage of adenosine A3 receptor antagonist will be dependent on the condition being treated, the subject being treated, for example, age, weight, and prior medical history, the route of administration, the form of the composition, the judgment of the physician, etc. According to some embodiments, the adenosine A3 receptor antagonist can be administered in an amount of about 0.001 µg to about 1 mg, alternatively of about 0.01 µg to 100 µg, or of about 1 µg to 10 µg per 1 $cm^2$ of skin that is the target of treatment.

The term "about" refers to a value which is 10% above or below the indicated value.

The present invention provides kits comprising the composition of the present invention suitable for injection and a syringe or an injection device.

Methods of Use

The present invention provides a method of promoting expression of collagen in aging skin comprising administering locally to an area of the aging skin of a subject a cosmetic or dermatological composition comprising an effective amount of an adenosine A3 receptor antagonist and a dermatologically acceptable carrier, thereby promoting the expression of collagen in the area of said aging skin.

The present invention further provides a method of treating a wound comprising administering locally to a wound site of a subject in need of such treatment a pharmaceutical composition comprising an effective amount of an adenosine A3 receptor antagonist and a pharmaceutically acceptable carrier, thereby treating the wound.

The present invention provides methods for improving the appearance of aging skin comprising administering locally to an area of aging skin of a subject a cosmetic or dermatological composition comprising an effective amount of an adenosine A3 receptor antagonist and a dermatologically acceptable carrier, wherein aging of the skin is associated with or affected by a decrease in collagen content in said skin, thereby improving the appearance of the aging skin.

Aging skin is characterized by thinning of the stratum corneum, degradation of collagen and elastin, lower synthesis of collagen and elastin, and thinning of the dermis, to list some, which eventually lead to wrinkling and skin atrophy.

The term "promoting expression of collagen in skin" means increasing the content of collagen, particularly collagen-1, in skin fibroblasts and/or in the extracellular matrix (ECM) of skin, e.g., dermis. Increasing the content of collagen can be the result of decreasing or preventing collagen degradation in skin fibroblasts and/or in the ECM, increasing collagen synthesis in skin fibroblasts, increasing collagen deposition in the ECM, or any combination thereof.

The term "improving the appearance of aging skin" means effecting one or more benefits in skin texture and/or feel. Benefits include, but are not limited to, decreasing or diminishing wrinkles, fine lines, and/or coarse deep lines; reducing loss of skin firmness; reducing skin thinning; reducing skin sagging. These benefits also include preventing or delaying the appearance of wrinkles, fine lines, and/or coarse deep lines; delaying or preventing loss of skin firmness; delaying or preventing skin thinning; delaying or preventing skin sagging. Other benefits include increasing the content of collagen fibers in skin; attenuating or preventing other histological changes in the stratum corneum, epidermis and/or dermis.

The methods of the present invention can therefore be useful for providing a smoother, more even appearance and/or feel of the skin and/or for increasing skin firmness or tightness and/or for imparting youthful appearance to skin so as to improve the appearance of aging skin, e.g., wrinkled skin, saggy skin, wizened skin, flaccid skin and/or thinned skin. The methods of the present invention do not encompass treating hyper-pigmented skin conditions.

The terms "administering locally" or "local administration" mean topical application on the surface of the skin, e.g., aging skin or wounded skin. Local administration also encompasses administration of the composition by injection, particularly by intraepidermal injection and/or intradermal injection and/or subdermal injection and/or subcutaneous injection and/or micro-injection.

The term "effective amount" is that amount of the active agent which is sufficient to provide a beneficial effect to the subject to which the composition is administered.

The effect of an adenosine A3 receptor antagonist on increasing the expression of collagen in skin can be determined by methods known in the art. As exemplified in the Examples herein below, skin explants can be subjected to collagen staining by antibodies against collagen-1. Alternatively, cells of skin samples can be isolated and subjected to collagen staining by antibodies against collagen-1.

The effect of an adenosine A3 receptor antagonist on wrinkles can be evaluated using hairless mice exposed to chronic solar-simulating ultraviolet (UV) irradiation (see, for example, U.S. Pat. No. 8,088,369 and WO 2008/001921). Mechanical and optical methods can also be used to measure wrinkles. Non-limiting examples of such instruments and methods include PRIMOS high resolution (GFMesstechnik, Germany) which can quantify periorbital wrinkles, perioral wrinkles (around mouth and lips), nasiolabial wrinkles (cheek, forehead wrinkles, and/or frowning wrinkles), and glabella wrinkles (between the eye brows) by optical 3D measurement of the skin; and Antera 3D® (Miravex Limited, Ireland) which allows for a view of skin in 2 and 3 dimensions as well as multi-spectral analysis of epidermis and dermis. The scan can provide information on how rough the skin is and how deep the wrinkles are. FOITS (Fast Optical in vivo Topometry of Human Skin) (Schrader Institute, Germany) is a non-contact method of 3D wrinkle analysis. This 3D wrinkle method allows for quantification of the surface topography of the skin and excludes skin color tone and surface reflection artifacts. The in-vivo 3D Breuckmann scanner (AICON, Michigan, USA) uses an imaging metrology principle based on structured light projection, and a combination of Gray Code and Phase shift technology. The Visioscan® (Courage+Khazaka electronic GmbH, Germany) uses a UVA-light video camera with high resolution to study the skin surface directly. The images show the structure of the skin and the level of dryness of the skin. The software analyses the grey level distribution and allows for the calculation of four clinical parameters to quantitatively and qualitatively describe the skin surface as an index: skin smoothness, skin roughness, scaliness, and wrinkles.

According to some embodiments, the area of aging skin to be treated is facial skin, neck skin, hand skin, and/or any other area of skin of which the appearance is desired to be improved. According to additional embodiments, facial skin is selected from the group consisting of the forehead, periorbital, chin, periorbital, nose, and cheek skin.

The aging skin to be treated includes one or more signs of skin aging including, but not limited to, wrinkles, fine lines, deep lines, saggy skin, uniform skin, flaccid skin, wizened skin, thinned skin, and any combination thereof.

According to some embodiments, improving the appearance of aging skin is reflected by a decrease in the number of wrinkles by at least about 10%, 20%, 30%, 40%, 50%, 60%, 70%, 80%, or by at least about 90%, or any integer in-between.

The compositions of the present invention are suitable for administration by topical or injectable route of administration (in particular intraepidermal and/or intradermal and/or subcutaneous injection and/or micro-injection).

Such compositions can be therefore useful to prevent or reduce wrinkles, in particular deep wrinkles and/or fine lines and/or to tighten the skin. In an embodiment wherein the composition of the invention is injected (in particular by micro-injection), it can be used for filling wrinkles and fine lines. In this embodiment, the composition may additionally comprise or be used in combination with filler products, particularly resorbable products such as hyaluronic acid, fats, collagen or proteins; or non-resorbable agents such as polyacrylamide gels or silicones. It may also be used to regenerate or strengthen the dermal-epidermal junction. It may be used to stimulate skin cells (in particular keratinocytes and/or fibroblasts), for example, by increasing their cell migration and/or synthesis of structural macromolecules, in particular collagen. Such compositions therefore make it possible to strengthen the dermis and/or epidermis, and/or to enhance the thickness thereof.

The methods of the present invention include administering locally the composition to a previously identified area of aging skin. Alternatively or additionally, the methods can include administering locally the composition to an area where one seeks to prevent the appearance of aging skin. While the methods include administering the composition to a previously identified area, such administering can be performed to a larger area, such as an area which includes healthy, un-wounded skin.

Many regimens exist for the administration of the composition. The composition can be applied at least once a day, twice a day, or on a more frequent daily basis, during a treatment period. When applied twice daily, the first and second applications can preferably be separated by at least 1 to 12 hours. Thus, the composition can be applied in the morning and/or in the evening before bed.

The treatment period is ideally of sufficient time to provide an improvement in the appearance of aging skin. The treatment period can be at least 1 week, and in some embodiments the treatment period can last about 4 weeks, 8 weeks, or 12 weeks. In certain embodiments, the treatment period will extend over multiple months (i.e., 3-12 months) or multiple years. In one embodiment, the cosmetic composition is applied at least once a day during a treatment period of at least 4 weeks, 8 weeks, or 12 weeks. In one embodiment, the cosmetic composition is applied twice a day during a treatment period of at least 4 weeks, 8 weeks, or 12 weeks. Alternatively, the cosmetic composition is administered once every other day, once every three days, once a week for a week, a month, or so long as the appearance of the aging skin is achieved.

While the subject for the cosmetic methods may be of any suitable age, the subject is, in some embodiments, an adult or a geriatric subject.

The cosmetic composition suitable for topical administration may be used in combination with mechanical devices, such as massage-roller devices having a mechanical and rubbing action to facilitate penetration of the active agent, or wave-emitting systems (light, low frequencies, infrared frequencies, etc.) which activate the response of the skin.

The compositions of the invention suitable for injection, in particular for intraepidermal and/or intradermal and/or subcutaneous injection and/or micro-injection, can be injected by a device comprising a needle or microneedle or by a needle-free injection device. Such devices are well known in mesotherapy. Alternatively, the compositions can be administered by means of iontophoresis directly in the area of the aging skin to achieve a greater penetration of the active agent.

The term "wound" as used herein refers broadly to injuries to the skin and subcutaneous tissue initiated in any one of a variety of ways (e.g., pressure sores from extended bed rest, wounds induced by trauma, wounds received during or following a surgical procedure, and the like) and with varying characteristics. Exemplary examples include, but are not limited to, burn wounds, incisional wounds, excisional wounds, wounds, ulcers, venous stasis ulcers, diabetic ulcers, and decubitus (pressure) ulcers. The normal repair process of wound healing typically includes four stages: (1) clotting/hemostasis stage; (2) inflammatory stage; (3) tissue cell proliferation stage; and (4) tissue cell remodeling stage.

The term a "chronic wound" refers to a wound that has failed to proceed through the orderly and timely stages to produce a durable structural, functional, and/or cosmetic closure as wounds do. Chronic wounds can stall in one or more stages, inefficiently or ineffectively complete one or more stages, skip one or more stages, or never reach one or more stages of the wound healing process such that the wounds do not proceed through the normal repair process of wound healing. In chronic wounds the balance between production and degradation of molecules such as collagen is lost and degradation plays too large a role. This is in contrast to acute wounds in which a precise balance between production and degradation of collagen exists. Wounds that do not heal within three months are considered chronic or hard to heal wounds. Chronic wounds may affect only the epidermis and dermis, however, they may affect deeper tissues, i.e., tissues all the way to the fascia.

The terms "treat," "treating," and "treatment" are all intended to refer to an amelioration or reversal of at least one measurable physical parameter related to a wound, e.g., a chronic wound. For example, the surface area of a chronic wound is a measurable physical parameter that can be determined before and after treatment to evaluate the effect of the treatment on the chronic wound. The terms "treat," "treating," and "treatment" can refer to improving the progression of wound healing, such as increasing the rate of wound healing. In one embodiment, "treat," "treating," and "treatment" refer to a reduction or an alleviation of one more symptoms associated with a wound, e.g., a chronic wound, such bleeding, swelling, or pain in the wound area. In another embodiment, "treat," "treating," and "treatment" refer to complete healing/closure of a wound, e.g., a chronic wound.

According to some embodiments, the wound to be treated by the pharmaceutical composition of the present invention is a chronic wound. According to further embodiments, the chronic wound is selected from the group consisting of a diabetic ulcer, a venous stasis ulcer, an arterial insufficiency ulcer, a pressure ulcer, a chronic post-operative wound, and a chronic post trauma wound.

Typically, administering the pharmaceutical composition for treating a wound is performed by topical application. According to some embodiments, the pharmaceutical composition is administered/applied once a day or twice a day for at least one day, at least one week, for at least one month, or so long as the treatment of the wound, i.e., wound healing/closure, is achieved. Alternatively, the pharmaceutical composition is administered/applied once every other day, once every three days, once a week for a week, a month, or so long as the treatment of the wound is achieved.

The method of treating a wound of the present invention is useful for a human subject as well as for any mammal including, but not limited to, dogs, cats, horses, cows, sheep, and pigs.

According to another aspect, the present invention provides a method of increasing migration of a skin cell comprising contacting the skin cell with an adenosine A3 receptor antagonist in an amount effective to increase migration of said skin cell, wherein the skin cell is a keratinocyte cell, a fibroblast cell, or a combination thereof, thereby increasing the migration of the skin cell. According to some embodiments, the adenosine A3 receptor antagonist and the skin cell is a skin cell of aging skin are as detailed herein above.

It is noted that each possibility disclosed throughout the specification represents a separate embodiment of the present invention.

Example 1

Adenosine A3 Receptors are Expressed on the Surface of Human Keratinocytes

The presence of adenosine A3 receptors (A3AR) in keratinocytes was first evaluated.

For that end, human keratinocyte cells—HaCaT cells, were incubated with rabbit anti human A3AR antibodies and then with Alexa Fluor® 488-conjugated goat anti-rabbit antibodies.

Figure 1:
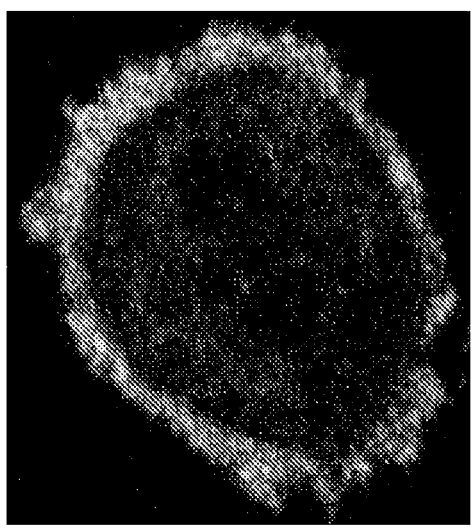
FIG. 1 demonstrates the expression of adenosine A3 receptors (A3AR) in keratinocytes. Confocal fluorescence image of A3AR (green) in HaCaT keratinocyte cells is shown.

As shown in FIG. 1, direct immunocytochemical labeling with anti-A3AR antibodies indicated the presence of adenosine A3 receptors in HaCaT cells, suggesting that A3AR antagonists may directly affect human keratinocytes.

Example 2

Expression of PAR-2 in keratinocytes PAR-2 is a differentiation marker in keratinocytes and was shown to be involved in melanosome uptake. It is known to be associated with terminal differentiation of the epidermis and sweat glands (Shin, Y. S. et al., Ann. Dermatol. (2015) 27(4): 364-370). Choi et al demonstrated that melanosome uptake was higher in differentiating keratinocytes as compared to non-differentiating keratinocytes and that the melanosome uptake was inhibited significantly by PAR-2 inhibitor (Choi, et al., Arch Dermatol Res (2014) 306: 59).

The presence of PAR-2 in keratinocytes was next examined.

HaCaT cells were incubated with rabbit anti human PAR-2 antibodies and then with Cye 5 goat anti-rabbit antibodies. As shown in FIG. 2, direct immunocytochemical labeling with anti-PAR-2 antibodies indicated the presence of PAR-2 in human keratinocytes.

Example 3

Cell Viability of Keratinocytes and Fibroblasts Treated with MRS-1523

The effect of MRS-1523 on keratinocyte (HaCaT) and fibroblast (3T3) cell viability was next examined.

HaCaT cells or 3T3 cells ($2\times10^4$) were incubated in 96-well Elisa plates in DMEM containing 10% fetal calf serum (FCS) in the presence of increasing concentrations of MRS-1523 for 24 hours. Cell viability was then measured using Alamar blue (AB) assay according to the manufacturer's instructions. Briefly, the cells were rinsed with PBS, and 0.2 ml of an AB solution (10% (v/v) of AB dye in DMEM) were added to each well. After incubation of 3 hours, AB fluorescence was quantified at the excitation and emission wavelengths of 540 and 595 nm, respectively, using a Tecan Genios microplate reader. The results are given as mean±SD. Statistical significance was determined by Student T-Test.

Figures 3A, 3B:
FIGS. 3A-C show bar graphs of the survival of HaCaT keratinocyte cells (A), 3T3 fibroblast cells (B), and B16-F1 melanocytes (C) after 24 hour-treatment with the adenosine A3 receptor antagonist, MRS-1523. *$p<0.05$, $p<0.01$, * $p<0.001$ by Student T-test.

FIG. 3A shows that MRS-1523 was toxic for kertinocytes only at high concentrations, i.e., 100 μM, while at concentrations of 10 μM or at lower concentrations, MRS-1523 significantly stimulated kertinocyte proliferation (by 8-16%).

FIG. 3B shows that MRS-1523 did not induce any toxic effect on fibroblasts. As shown in FIG. 3B, MRS-1523 exerted slight but significant increase in fibroblast proliferation at a concentration of 10 μM.

Figure 3C:
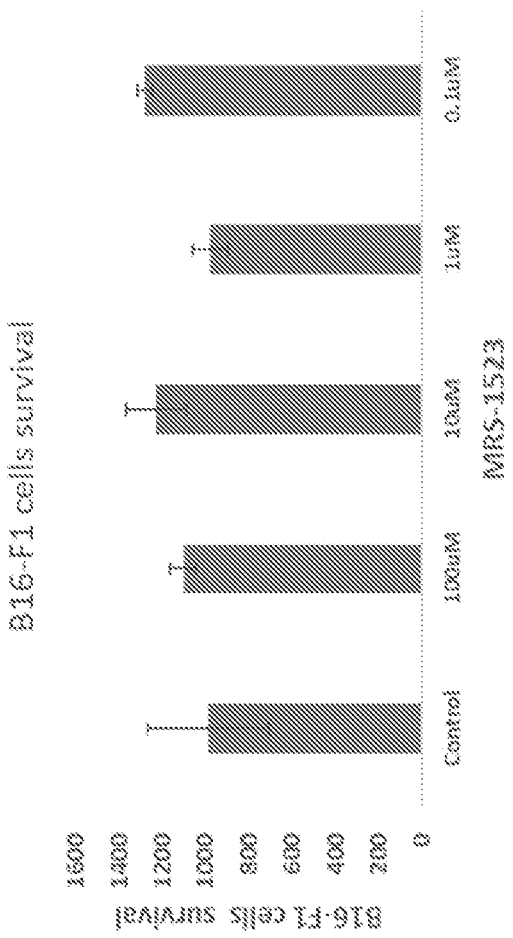

FIG. 3C shows that MRS-1523 did not induce any toxic effect on B16-F1 melanocyte cells, but rather promoted their proliferation.

Taken together, these results indicated that MRS-1523 stimulates keratinocyte proliferation at concentrations of 10 μM or lower, and that it has less prominent effect on fibroblast or melanocyte proliferation.

Example 4

Migration of Keratinocytes and Fibroblasts Treated with MRS-1523

Cell migration is essential in wound healing and in treating wrinkles. Gap closure presented by the gap size represents the ability of cells to migrate and thereby to reach sites where their function is required. The effect of MRS-1523 on keratinocyte or fibroblast migration in a scratch assay was next examined.

Keratinocyte HaCaT cells or 3T3 fibroblast cells ($10^6$ cells) were grown in 35 mm petri dishes in DMEM containing 10% FCS overnight. Thereafter, the cell cultures were scratched using 20 μl pipet tip in the middle of the culture plate, the cells were washed three times, and then MRS-1523 (at concentrations of 10 nM to 10 μM in DMEM containing 10% FCS) was added to each scratched plate and incubated with the cells for 24 hours. The gap size in plates of MRS-1523 treated cells was compared to the gap size in plates of control cells which were scratched and incubated for 24 hours in DMEM containing 10% FCS in the absence of MRS-1523. The results are presented as mean±SD. Statistical significance was determined by Student T-test.

Figures 4A, 4B:
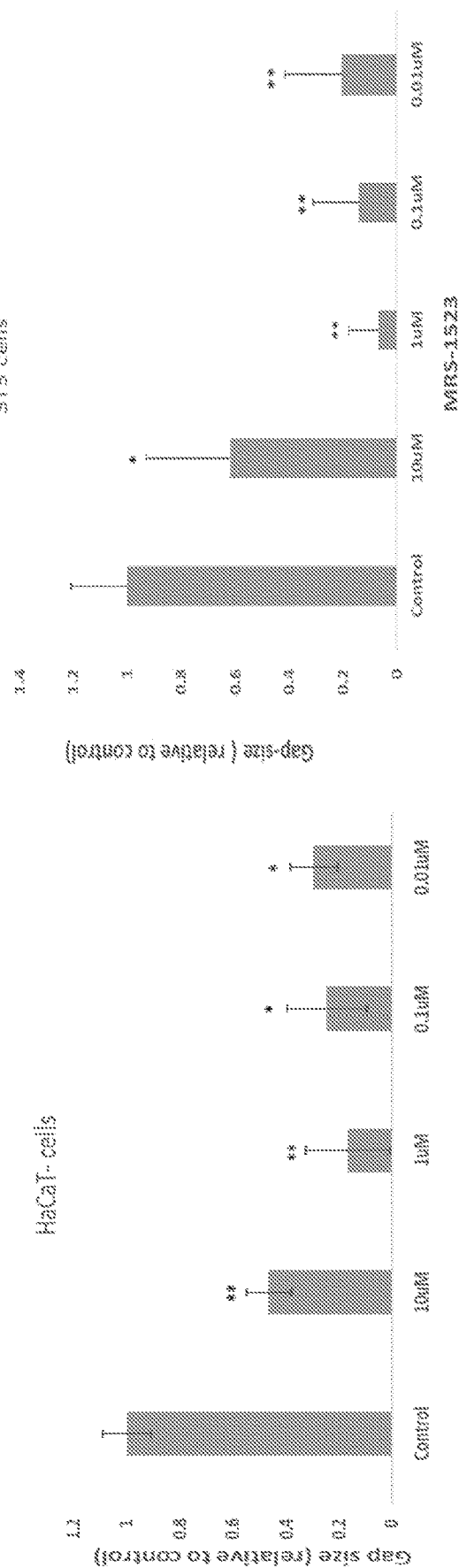
FIGS. 4A-E show bar graphs of the gap size in a scratch assay of different cell types in culture.
Figures 4C, 4D, 4E:
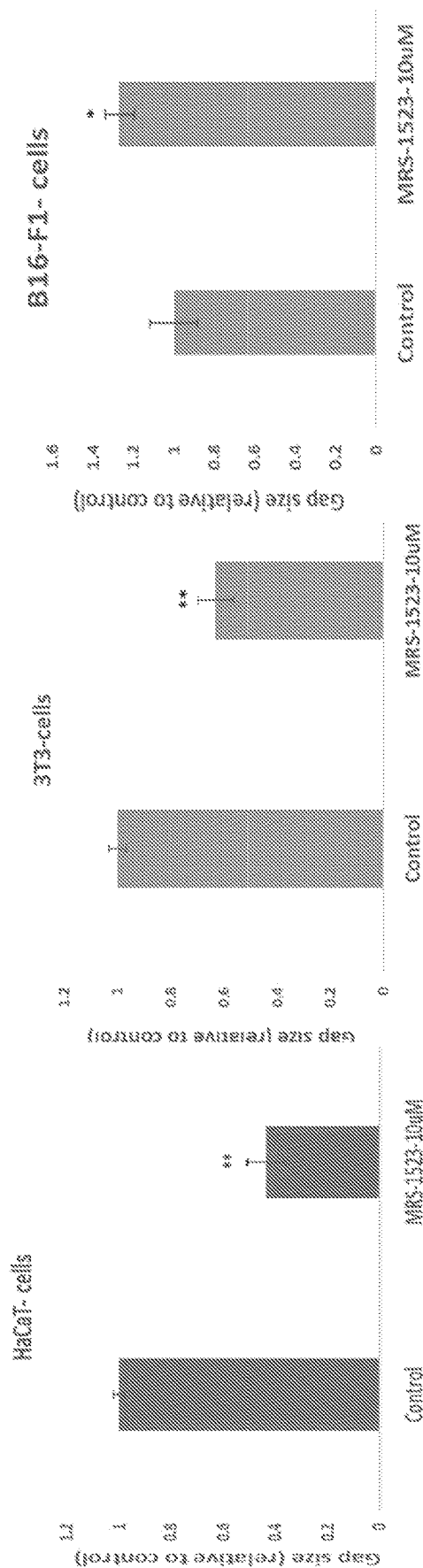

FIGS. 4A-B show that treatment of keratinocytes or fibroblasts with low concentrations of MRS-1523 (0.01 μM-10 μM) caused a significant reduction in the gap size as compared to control cells, thus indicating that this antagonist increases HaCaT (FIG. 4A) and fibroblast 3T3 (FIG. 4B) cell migration. Moreover, MRS-1523 at a concentration of 10 μM significantly stimulated HaCaT (FIG. 4C) and 3T3-fibroblast cell migration (FIG. 4D), but attenuated melanocytes migration (FIG. 4E).

Taken together, these results indicated that MRS-1523 at low concentrations of 10 M or below can be highly useful in treating aging skin, e.g., wrinkles, and in wound healing with essentially no adverse effects, i.e., toxicity. In addition, due to its attenuating effect on melanocyte migration, MRS-1523 can be even more advantageous as it can prevent undesired hyperpigmentation of the wound area or of the sites of treated wrinkles.

Example 5

Increase in Fibroblast and Collagen Levels in Skin Explants Treated with MRS-1523

Activation of fibroblasts in the dermis and production of collagen is essential in diminishing wrinkles in anti-aging treatments as well as in wound healing.

Figure 5A:
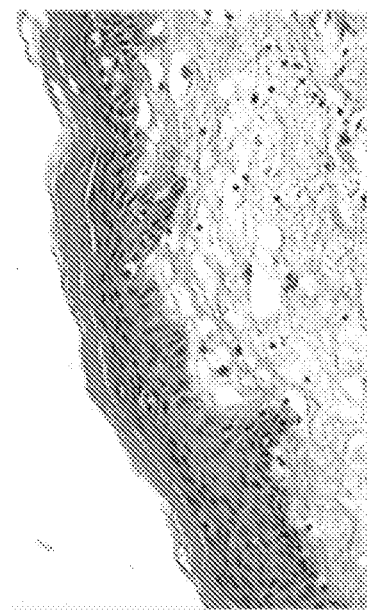
FIGS. 5A-D show fibroblast and collagen staining of histological sections of skin explants treated with 10 μM MRS-1523 for 12 days.

Skin explants were treated with MRS-1523 (10 μM) for 12 days. Thereafter, the skin explants were stained with hematoxylin and eosin (H&E; FIGS. 5A and 5C) or with Fontana-Masson (FIGS. 5B and 5D).

Figure 5B:
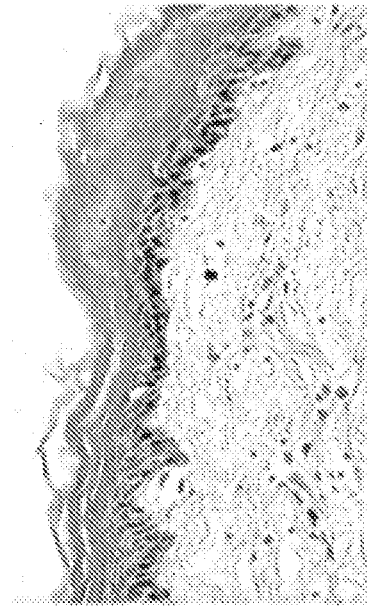
Figure 5C:
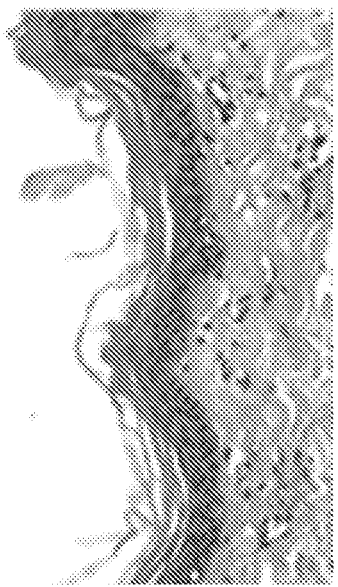
Figure 5D:
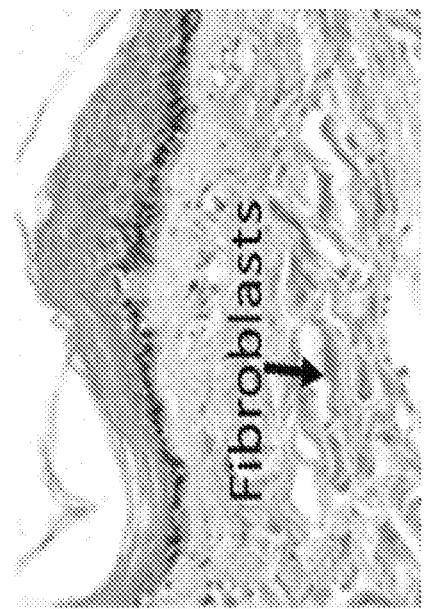

FIGS. 5C and 5D show an increase in both fibroblast and collagen levels in the dermis of skin explants treated with MRS-1523 as compared to untreated skin explants (FIGS. 5A and 5B). These results therefore indicated that not only does MRS-1523 increase fibroblast abundance in skin explants, but also induces collagen deposition in the ECM of the treated skin explants.

Example 6

Increase in Collagen Level in Fibroblasts Treated with MRS-1523

The effect of MRS-1523 on collagen level in fibroblasts in culture was next examined. 3T3-fibroblast cells were grown in DMEM containing 10% FCS for 24 hours, and then were treated with 10 μM MRS-1523 for additional 24 hours. Thereafter, the presence of collagen or F-actin was evaluated as follows: the cells were incubated with rabbit anti-collagen-1 antibodies, and then with Alexa Fluor® 488-conjugated goat anti-rabbit antibodies to detect collagen-1 (green staining). Detection of F-actin was performed by F-actin-Phalloidin-staining (red staining). Cell nuclei were stained with 4',6-diamidino-2-phenylindole (DAPI; blue staining).

Confocal fluorescence images of collagen-1 (FIGS. 6B and 6E) show the increased expression of collagen-1 in 3T3-fibroblast cells treated with MRS-1523 (FIG. 6E) as compared to control untreated fibroblasts (FIG. 6B). Expression of F-actin was not increased in response to MRS-1523 treatment (FIG. 6F) as compared to control cells (FIG. 6C), indicating that the effect of MRS-1523 on increasing collagen-1 expression was specific. FIGS. 6A and 6D show nuclei staining of control untreated cells and MRS-1523 treated cells.

Example 7

Decrease in Differentiation Markers in HaCaT Cells Treated with MRS-1523

Differentiation of cells is known to attenuate their proliferation and migration. In order to evaluate the effect of MRS-1523 on keratinocyte differentiation, the expression of different differentiation markers in keratinocytes treated with MRS-1523 was determined.

HaCaT cells were grown in DMEM containing 10% FCS for 24 hours. The cells were then treated with 10 μM MRS-1523 for 24 hours, washed with PBS, and fixed with 4% paraformaldehyde for 1 hour. Fixed cells were washed and incubated with the following primary antibodies (Sigma): anti-PAR-2 (Clone SAM11 produced in mouse, reactive to mouse and human) followed by secondary antibodies, anti-mouse antibodies conjugated to FITC, or anti-Filaggrin (FLG; produced in rabbit) followed by secondary antibodies, anti-rabbit antibodies conjugated to Alexa Fluor® 488.

Figure 7A:
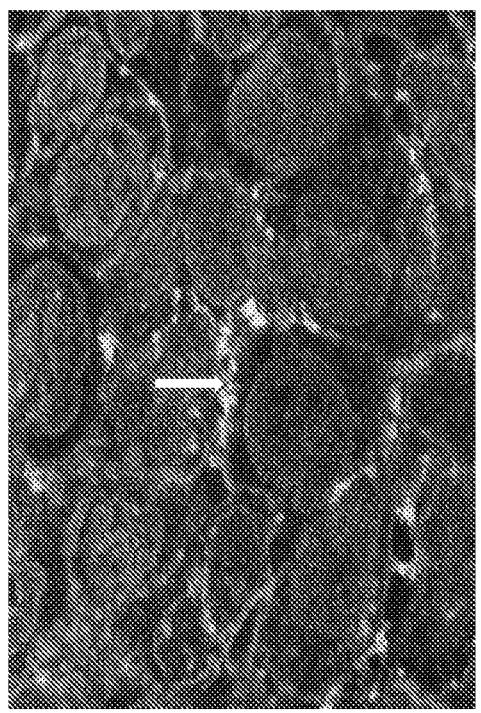
FIGS. 7A-D show the decrease in expression of two differentiation markers in HaCaT cells treated with 10 μM MRS-1523 as compared to control untreated cells. Control untreated HaCaT cells or HaCaT cells treated for 24 hours with MRS-1523 were stained for the expression of Protease activated receptor-2 (PAR-2.
Figure 7B:
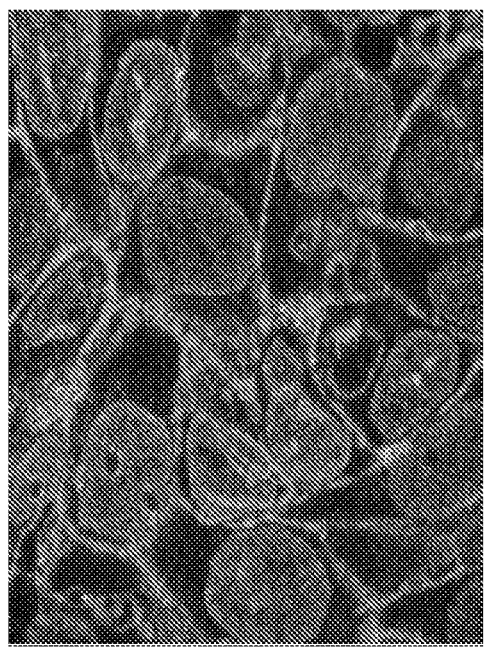
Figure 7D:
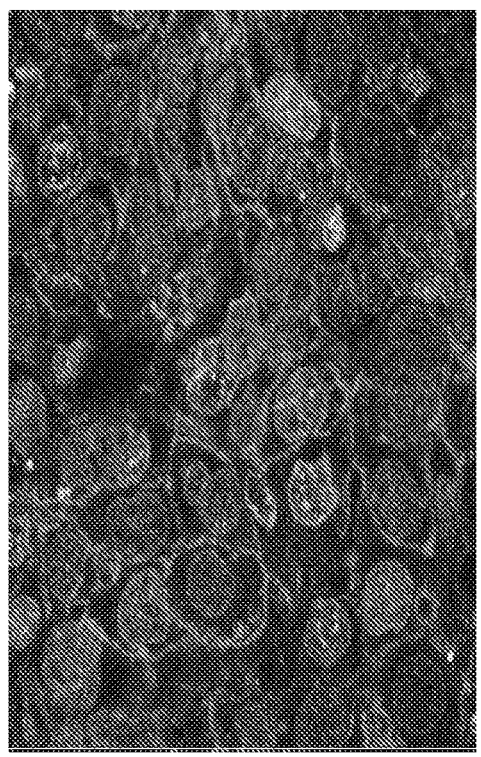
Figure 7C:
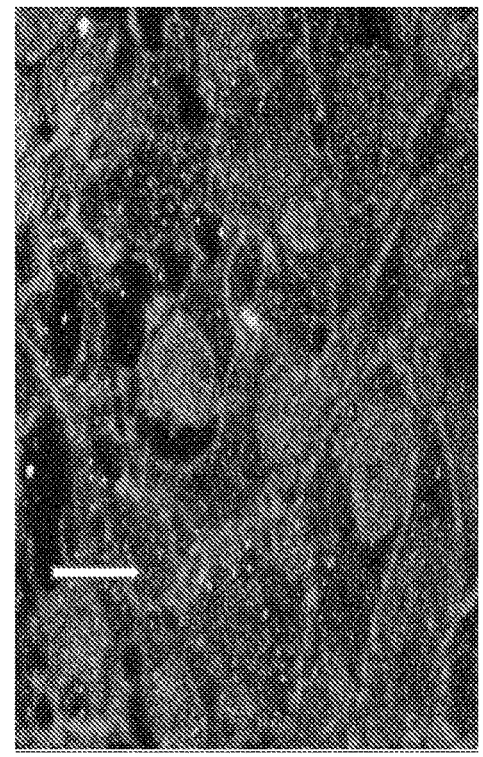

As shown in FIGS. 7A-D, MRS-1523 decreased the differentiation of HaCaT cells as detected by the decrease in the expression of PAR-2 (FIG. 7B) and Filaggrin (FLG; FIG. 7D) as compared to the expression of PAR-2 and FLG in control untreated HaCaT cells (FIGS. 7A and 7C, respectively).

Taken together, these results indicated that MRS-1523, particularly at low concentrations of 10 μM or below, is capable of: increasing the migration of keratinocytes and fibroblasts; increasing keratinocyte proliferation; decreasing keratinocyte differentiation; increasing the production of collagen by fibroblasts and its deposition in the ECM; increasing the abundance of fibroblasts; and decreasing the migration of melanocytes. Thus, MRS-1523 can be highly useful in promoting wound healing and in treating aging skin, e.g., wrinkles, while avoiding toxic effects on keratinocytes and fibroblasts, and reducing or eliminating undesired hyperpigmentation of the wound sites and wrinkles.

It will be appreciated by persons skilled in the art that the present invention is not limited by what has been particularly shown and described herein above. Rather the scope of the invention is defined by the claims that follow.

What is claimed is:

1. A method of promoting expression of collagen in aging or damaged skin comprising administering locally to an area of the aging or damaged skin of a subject a composition comprising an effective amount of an adenosine A3 receptor antagonist and an acceptable carrier, wherein the adenosine A3 receptor antagonist is selected from the group consisting of 3-propyl-6-ethyl-5 [(ethylthio) carbonyl]-2-phenyl-4-propyl-3-pyridine carboxylate (MRS-1523); 1,4-dihydro-2-methyl-6-phenyl-4-(phenylethynyl)-3,5-pyridinedicarboxylic acid 3-ethyl-5-[(3-nitrophenyl) methyl] ester (MRS-1334); 3-ethyl-5-benzyl-2-methyl-4-phenylethynyl-6-phenyl-1,4-(±)-dihydropyridine-3,5 dicarboxylate (MRS-1191); and 3-ethyl-5-benzyl-2-methyl-6-phenyl-4-styryl-1,4-(±)-dihydropyridine-3,5-dicarboxylate (MRS-1097), thereby promoting the expression of collagen in the area of said aging or damaged skin, wherein the promotion of expression of collagen in said aging or damaged skin improves the appearance of the aging or damaged skin in the areas where the composition is administered.

2. A method for treating damaged skin of a chronic wound site of a subject comprising administering locally to the chronic wound site a composition comprising an effective amount of an adenosine A3 receptor antagonist and an acceptable carrier, thereby promoting the expression of collagen in the damaged skin to treat the chronic wound; wherein the adenosine A3 receptor antagonist is selected from the group consisting of 3-propyl-6-ethyl-5[(ethylthio) carbonyl]-2-phenyl-4-propyl-3-pyridine carboxylate (MRS-1523); 1,4-dihydro-2-methyl-6-phenyl-4-(phenylethynyl)-3,5-pyridinedicarboxylic acid 3-ethyl-5-[3-nitrophenyl) methyl] ester (MRS-1334); 3-ethyl-5-benzyl-2-methyl-4-phenylethynyl-6-phenyl-1,4-(*)-dihydropyridine-3,5 dicarboxylate (MRS-1191); and 3-ethyl-5-benzyl-2-methyl-6-phenyl-4-styryl-1,4-(*)-dihydropyridine-3,5-dicarboxylate (MRS-1097); and
wherein the chronic wound is selected from the group consisting of a diabetic ulcer, a venous stasis ulcer, an arterial insufficiency ulcer, a pressure ulcer, a chronic post-operative wound, and a chronic post trauma wound.

3. The method according to claim 2, wherein the pharmaceutical composition is in the form selected from the group consisting of a solution, emulsion, nano emulsion, suspension, microparticles, ointment, cream, lotion, paste, gel, hydrogel, spray, powder, stick, and a patch.

4. The method according to claim 2, wherein the pharmaceutical composition is administered topically.

5. The method according to claim 1, wherein the skin is aging facial skin, neck skin, or a combination thereof.

6. The method according to claim 1, wherein the skin is aging skin selected from the group consisting of wrinkled skin, wizened skin, slaggy skin, thinned skin, and any combination thereof.

7. The method according to claim 6, wherein the wrinkled skin is selected from the group consisting of skin comprising wrinkles, skin comprising fine lines, skin comprising coarse deep lines, and any combination thereof.

8. The method according to claim 1, wherein the adenosine A3 receptor antagonist is 3-propyl-6-ethyl-5 [(ethylthio) carbonyl]-2-phenyl-4-propyl-3-pyridine carboxylate (MRS-1523).

9. The method according to claim 2, wherein the adenosine A3 receptor antagonist is 3-propyl-6-ethyl-5 [(ethylthio) carbonyl]-2-phenyl-4-propyl-3-pyridine carboxylate (MRS-1523).

10. The method according to claim 1, wherein the adenosine A3 receptor antagonist is administered in a cosmetic or dermatological composition that further comprises one or more excipients selected from the group consisting of emulsifying agents, pH buffering agents, preservatives, chelating agents, tonicity agents, humectants, antioxidants, and gelling agents.

11. The method according to claim 10, wherein the cosmetic or dermatological composition is in the form selected from the group consisting of a solution, emulsion, nanoemulsion, suspension, microparticles, ointment, cream, lotion, paste, gel, hydrogel, spray, powder, stick, and a patch.

12. The method according to claim 10, wherein the cosmetic or dermatological composition is administered topically.

13. The method according to claim 10, wherein the cosmetic or dermatological composition is administered by injection.

14. The method according to claim 13, wherein the injection is intraepidermal injection, intradermal injection, subcutaneous injection, micro-injection, or any combination thereof.

* * * * *